United States Patent
Kong et al.

(10) Patent No.: US 11,981,898 B2
(45) Date of Patent: May 14, 2024

(54) GENE EDITING METHODS WITH INCREASED KNOCK-IN EFFICIENCY

(71) Applicant: APPLIED STEMCELL, INC., Milpitas, CA (US)

(72) Inventors: Lingjie Kong, Union City, CA (US); Alfonso Farruggio, Stanford, CA (US); Andrew Hilmer, Hayward, CA (US); Padmaja Tummala, Santa Clara, CA (US); Ruby Yanru Tsai, San Jose, CA (US)

(73) Assignee: APPLIED STEMCELL, INC., Milpitas, CA (US)

( * ) Notice: Subject to any disclaimer, the term of this patent is extended or adjusted under 35 U.S.C. 154(b) by 349 days.

(21) Appl. No.: 16/622,948

(22) PCT Filed: Jun. 18, 2018

(86) PCT No.: PCT/US2018/037964
§ 371 (c)(1),
(2) Date: Dec. 16, 2019

(87) PCT Pub. No.: WO2018/232382
PCT Pub. Date: Dec. 20, 2018

(65) Prior Publication Data
US 2021/0147856 A1    May 20, 2021

Related U.S. Application Data

(60) Provisional application No. 62/521,280, filed on Jun. 16, 2017.

(51) Int. Cl.
*C12N 15/66* (2006.01)
*C12N 9/22* (2006.01)
*C12N 15/113* (2010.01)

(52) U.S. Cl.
CPC ............ *C12N 15/66* (2013.01); *C12N 9/22* (2013.01); *C12N 15/113* (2013.01); *C12N 2310/315* (2013.01); *C12N 2310/321* (2013.01); *C12Y 301/00* (2013.01)

(58) Field of Classification Search
CPC ............ C12Q 1/6806; C12Q 2525/125; C12N 15/63; C12N 15/111; C12N 2310/321
USPC .............. 435/6.1, 91.1, 91.31, 455, 458; 514/44 A, 44 R; 536/23.1, 24.5
See application file for complete search history.

(56) References Cited

U.S. PATENT DOCUMENTS

| 7,897,747 B2 | 3/2011 | Mindrinos et al. |
| 2015/0252399 A1 | 9/2015 | Stadtmüller et al. |
| 2017/0029805 A1* | 2/2017 | Li .......................... A61P 31/00 |

FOREIGN PATENT DOCUMENTS

WO    2016205749 A9    12/2016

OTHER PUBLICATIONS

Turan et al. "Precise Correction of Disease Mutations in Induced Pluripotent Stem Cells Derived From Patients With Limb Girdle Muscular Dystrophy," Molecular Therapy, Feb. 26, 2016 (Feb. 26, 2016), vol. 24, Iss. 4, pp. 685-696. entire document.
International Search Report of PCT Application No. PCT/US2018/037964, dated Sep. 7, 2018.
Rolen M Quadros et al. "Easi-CRISPR: a robust method for one-step generation of mice carrying conditional and insertion alleles using long ssDNA donors and CRISPR ribonucleoproteins", Genome Biology (2017) 18:92, pp. 1-17.
Laia Civit et al. "Evaluation of techniques for generation of single-stranded DNA for quantitative detection", Analytical Biochemistry 431 (2012) 132-138.
First office action of the corresponding Chinese application No. 201880051502.3.

* cited by examiner

*Primary Examiner* — Jane J Zara
(74) *Attorney, Agent, or Firm* — Jun He Law Offices P.C; Yi Zhang

(57) ABSTRACT

The present disclosure provides compositions and methods for targeted insertion of a gene of interest in the genome of a cell using single-stranded DNA or double-stranded DNA with 3¡ overhang. Also provided are methods of generating single-stranded DNA or double-stranded DNA with 3' overhang that can be used for targeted insertion.

5 Claims, 2 Drawing Sheets
Specification includes a Sequence Listing.

GENE EDITING METHODS WITH INCREASED KNOCK-IN EFFICIENCY

CROSS-REFERENCE TO RELATED APPLICATIONS

This application is the national phase stage of PCT/US2018/037964 filed Jun. 18, 2018, which claims priority to U.S. provisional patent application No. 62/521,280, filed Jun. 16, 2017, the disclosure of which is incorporated herein by reference.

FIELD OF THE INVENTION

The present invention generally relates to methods for gene editing.

BACKGROUND

The development of gene editing technology using engineered site-specific nuclease (e.g., CRISPR, ZFN, TALEN) opens the doors for targeted gene modification in higher organisms including human and holds great potential for gene therapy. Such gene editing technology typically depends on the nuclease to create a DNA double-strand break (DSB) and the cellular DNA repair mechanism to generate targeted mutations or gene-insertions, i.e. knock-in. Precise site-specific insertion of a gene of interest usually happens through the homology directed repair (HDR) pathway, which has a low rate of recombination even in the existence of a DSB.

It has been reported that using single-stranded DNA (ssDNA) to provide a donor of gene of interest can increase the efficiency of targeted insertion through HDR (see, e.g., Quadros et al., "Easi-CRISPR: a robust method for one-step generation of mice carrying conditional and insertion alleles using long ssDNA donors and CRISPR ribonucleoproteins." Genome Biology (2017) 18:92). However, long ssDNA is unstable, and the size of ssDNA generated by chemical synthesis is limited to about 200 nucleotides.

Therefore, there is a continuing need for developing new gene-editing technology with increased insertion efficiency.

SUMMARY OF INVENTION

In one aspect, the present disclosure provides a composition for editing a target locus in a cell. In one embodiment, the composition comprises (i) a site-specific nuclease or a nucleic acid encoding the same; and (ii) a single-stranded DNA (ssDNA) comprising a gene of interest flanked by homologous arms complementary to the target locus, wherein the ssDNA has an exonuclease resistant modification.

In certain embodiments, the site-specific nuclease is Cas9, a zinc finger nuclease or a TALEN. In certain embodiment, the site-specific nuclease is Cas9 and the composition further comprises a guide RNA directed to the target locus.

In certain embodiments, the exonuclease resistant modification is biotinylation, 5' hydroxy group, phosphorothioate bond, 2'-O-methyl base or 2'fluoro base. In certain embodiments, the exonuclease resistant modification is resistant to lambda exonuclease, T5 exonuclease or T7 exonuclease.

In another embodiment, the composition provided herein comprises (i) a site-specific nuclease or a nucleic acid encoding the same; and (ii) a double-stranded DNA (dsDNA) consisting of first and second DNA strand, wherein the dsDNA comprises a gene of interest flanked by homologous arms complementary to the target locus, wherein the first DNA strand has a first single-stranded DNA (ssDNA) overhang at 3' end and the second DNA strand has a second ssDNA overhang at 3' end.

In certain embodiments, each of the first and second DNA strand has an exonuclease resistant modification. In certain embodiments, the exonuclease resistant modification is biotinylation, phosphorothioate bond, 2'-O-methyl or 2'fluoro base. In certain embodiments, the exonuclease resistant modification is resistant to lambda exonuclease, T5 exonuclease or T7 exonuclease.

In certain embodiments, each of the first and second ssDNA overhangs has a length of 5-200 nucleotides.

In another aspect, the present disclosure provides a method for inserting a gene of interest to a target locus in a cell. In certain embodiments, the method comprises introducing into the cell: (i) a site-specific nuclease or a nucleic acid encoding the same; and (ii) a single-stranded DNA (ssDNA) comprising a gene of interest flanked by homologous arms complementary to the target locus, wherein the ssDNA has one or more exonuclease resistant modifications.

In another embodiment, the method comprises introducing into the cell: (i) a site-specific nuclease or a nucleic acid encoding the same; and (ii) a double-stranded DNA (dsDNA) consisting of first and second DNA strand, wherein the first DNA strand has a first single-stranded DNA (ssDNA) overhang at 3' end and the second DNA strand has a second ssDNA overhang at 3' end.

In yet another aspect, the present disclosure provides a method for generating a ssDNA used in the methods provided herein. In certain embodiments, the method comprises: (1) amplifying a gene of interest using a pair of primers to generate a dsDNA amplicon, wherein one of the pair of primers has an exonuclease resistant modification that is resistant to an exonuclease; and (2) treating the dsDNA amplicon with the exonuclease, thereby generating a ssDNA comprising the gene of interest.

In certain embodiments, the exonuclease is lambda exonuclease, T5 exonuclease or T7 exonuclease.

In certain embodiments, the exonuclease resistant modification is biotinylation, 5' hydroxy group, phosphorothioate bond, 2'-O-methyl or 2'fluoro base.

In certain embodiments, the ssDNA further comprises homologous arms flanking the gene of interest.

In another aspect, the present disclosure provides a method for generating a double-stranded DNA with 3' single-stranded overhang that can be used in the methods provided herein. In certain embodiments, the method comprises: (1) amplifying a gene of interest using a pair of primers to generate a dsDNA amplicon, wherein each of the pair of primers has an exonuclease resistant modification that is resistant to an exonuclease; and (2) treating the dsDNA amplicon with the exonuclease, thereby generating a dsDNA consisting of first and second DNA strand, wherein the dsDNA comprises the gene of interest, wherein the first DNA strand has a first ssDNA overhang at 3' end and the second DNA strand has a second ssDNA overhang at 3' end.

In certain embodiments, the dsDNA further comprises homologous arms flanking the gene of interest.

In another embodiment, the method for generating a double-stranded DNA with 3' single-stranded overhang comprises annealing a first single-stranded DNA and a second single-stranded DNA, wherein each of the first and second ssDNA is generated according to the method provided herein.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

DESCRIPTION OF THE INVENTION

Figure 1:
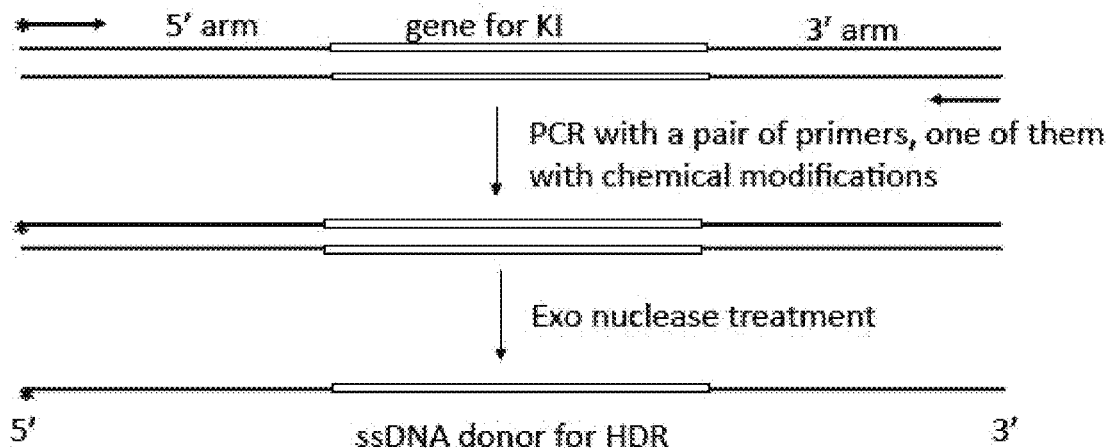
FIG. 1 illustrates an exemplary example of the methods for generating the ssDNA donor for targeted insertion.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The following definitions are provided to assist the reader. Unless otherwise defined, all terms of art, notations and other scientific or medical terms or terminology used herein are intended to have the meanings commonly understood by those of skill in the art. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

As used herein, a "Cas protein" refers to a polypeptide that binds to the guide RNA and exhibit nuclease activity. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. These enzymes are known; for example, the amino acid sequence of S. pyogenes Cas9 protein may be found in the SwissProt database under accession number Q99ZW2. In some embodiments, the unmodified Cas protein has DNA cleavage activity. In some embodiments, the Cas protein directs cleavage of one or both strands at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, the Cas protein is mutated such that the mutated Cas protein lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A.

As used herein, a "CRISPR-Cas guide RNA" or "guide RNA" or "gRNA" refers to an RNA that directs sequence-specific binding of a CRISPR complex to the target sequence. Typically, a guide RNA comprises (i) a guide sequence that has sufficient complementarity with a target polynucleotide sequence to hybridize with the target sequence and (ii) a trans-activating cr (tracr) mate sequence. A guide RNA may further comprises a tracr RNA fused at the 3' end, resulting a single chimeric guide RNA. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, an alveolar macrophage; a cell from circular system or organ, e.g., myocardiocyte and pericyte; a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula *densa* cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for mass bioproduction, e.g., CHO cells.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%>, 70%>, 80%>, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

The term "introduce" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon. The vector of the present disclosure may be introduced into a cell using any method known in the art. Various techniques for transforming animal cells may be employed, including, for example: microinjection, retrovirus mediated gene transfer, electroporation, transfection, or the like (see, e.g., Keown et al., Methods in Enzymology 1990, 185:527-537). In one embodiment, the vector is introduced to the cell via a virus.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, a "nuclease" is an enzyme capable of cleaving the phosphodiester bonds between the nucleotide subunits of nucleic acids. A "nuclease domain" is an independently folded protein domain having nuclease activity. A "site-specific nuclease" refers to a nuclease whose functioning depends on a specific nucleotide sequence. Typically, a site-specific nuclease recognizes and binds to a specific nucleotide sequence and cuts a phosphodiester bond within the nucleotide sequence. In certain embodiments, the double-strand break is generated by site-specific cleavage using a site-specific nuclease. Examples of site-specific nucleases include, without limitation, zinc finger nucleases (ZFNs), transcriptional activator-like effector nucleases (TALENs) and CRISPR (clustered regularly interspaced short palindromic repeats)-associated (Cas) nucleases.

A site-specific nuclease typically contains a DNA-binding domain and a DNA-cleavage domain. For example, a ZFN contains a DNA binding domain that typically contains between three and six individual zinc finger repeats and a nuclease domain that consists of the FokI restriction enzyme that is responsible for the cleavage of DNA. The DNA binding domain of ZFN can recognize between 9 and 18 base pairs. In the example of a TALEN, which contains a TALE domain and a DNA cleavage domain, the TALE domain contains a repeated highly conserved 33-34 amino acid sequence with the exception of the 12$^{th}$ and 13$^{th}$ amino acids, whose variation shows a strong correlation with specific nucleotide recognition. For another example, Cas9, a typical Cas nuclease, is composed of a guide RNA binding domain (Rec 1 domain), the PAM-interacting domain for initiating binding to target DNA, and two endonuclease domains (RuvC domain and HNH domain).

An "overhang" or "single-stranded overhang" as used herein refers to a stretch of unpaired nucleotides, i.e., single stranded nucleotides in the end of a nucleic acid, e.g., DNA molecule. A 3' overhang is an overhang protruding at the 3' end of the strand. A 5' overhang is an overhang protruding at the 5' end of the strand.

"Primer" as used herein refers to an oligonucleotide molecule with a length of 7-200 nucleotides, preferably 10-150 nucleotides, preferably 15-100 nucleotides, or 15-80 nucleotides, or 17-50 nucleotides. For example, the primer can an oligonucleotide having a length of 7, 8, 9, 10, 11, 12, 13, 14, 15, 16, 17, 18, 19, 20, 21, 22, 23, 24, 25, 26, 27, 28, 29, 30, about 40, about 50, about 60, about 70, about 80, about 90, about 100, about 120, about 140, about 160, about 180 or about 200 nucleotides. Primers are usually used in the amplification of a DNA sequence by polymerase chain reaction (PCR) as well known in the art. For a DNA template sequence to be amplified, a pair of primers can be designed at its 5' upstream and its 3' downstream sequence, i.e. 5' primer and 3' primer, each of which can specifically hybridize to a separate strand of the DNA double strand template. 5' primer is complementary to the anti-sense strand of the DNA double strand template; and 3' primer is complementary to the sense strand of the DNA template. As known in the art, the "sense strand" of a double stranded DNA template is the strand which contains the sequence identical to the mRNA sequence transcribed from the DNA template (except that "U" in RNA corresponds to "T" in the DNA) and encoding for a protein product. The complementary sequence of the sense strand is the "anti-sense strand."

As used herein, a "transcription activator-like effector nuclease" (TALEN) refers to an artificial restriction enzymes made by fusing a transcription activator-like effector (TALE) DNA-binding domain to a DNA cleavage domain (e.g., a nuclease domain), which can be engineered to cut specific sequences. TALEs are proteins that are secreted by *Xanthomonas* bacteria via their type III secretion system when they infect plants. TALE DNA-binding domain contains a repeated highly conserved 33-34 amino acid sequence with divergent 12th and 13th amino acids, which are highly variable and show a strong correlation with specific nucleotide recognition. The relationship between amino acid sequence and DNA recognition allows for the engineering of specific DNA-binding domains by selecting a combination of repeat segments containing the appropriate variable amino acids. The non-specific DNA cleavage domain from the end of the FokI endonuclease can be used to construct TALEN. The FokI domain functions as a dimer, requiring two constructs with unique DNA binding domains for sites in the target genome with proper orientation and spacing. See Boch, Jens "TALEs of genome targeting" Nature Biotechnology (2011) 29: 135-6; Boch, Jens et al., "Breaking the Code of DNA Binding Specificity of TAL-Type III Effectors" Science (2009) 326: 1509-12; Moscou M J and Bogdanove A J "A Simple Cipher Governs DNA Recognition by TAL Effectors" Science (2009) 326 (5959): 1501; Juillerat A et al., "Optimized tuning of TALEN specificity using non-conventional RVDs" Scientific Reports (2015) 5: 8150; Christian et al., "Targeting DNA Double-Strand Breaks with TAL Effector Nucleases" Genetics (2010) 186 (2): 757-61; Li et al., "TAL nucleases (TALNs): hybrid proteins composed of TAL effectors and FokI DNA-cleavage domain" Nucleic Acids Research (2010) 39: 1-14.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

As used herein, a "zinc finger nuclease" (ZFN) refers to an artificial restriction enzyme generated by fusing a zinc finger DNA-binding domain to a DNA-cleavage domain. Zinc finger domain can be engineered to target specific desired DNA sequences, which directs the zinc finger nucleases to cleave the target DNA sequences. Typically, a zinc finger DNA-binding domain contains three to six individual zinc finger repeats and can recognize between 9 and 18 base pairs. Each zinc finger repeat typically includes approximately 30 amino acids and comprises a $\beta\beta\alpha$-fold stabilized by a zinc ion. Adjacent zinc finger repeats arranged in tandem are joined together by linker sequences. Various strategies have been developed to engineer zinc finger domains to bind desired sequences, including both "modular assembly" and selection strategies that employ either phage display or cellular selection systems (Pabo C O et al., "Design and Selection of Novel Cys2His2 Zinc Finger Proteins" Annu. Rev. Biochem. (2001) 70:313-40). The most straightforward method to generate new zinc-finger DNA-binding domains is to combine smaller zinc-finger repeats of known specificity. The most common modular assembly process involves combining three separate zinc finger repeats that can each recognize a 3 base pair DNA sequence to generate a 3-finger array that can recognize a 9 base pair target site. Other procedures can utilize either 1-finger or 2-finger modules to generate zinc-finger arrays with six or more individual zinc finger repeats. Alternatively, selection methods have been used to generate zinc-finger DNA-binding domains capable of targeting desired sequences. Initial selection efforts utilized phage display to select proteins that bound a given DNA target from a large pool of partially randomized zinc-finger domains. More recent efforts have utilized yeast one-hybrid systems, bacterial one-hybrid and two-hybrid systems, and mammalian cells. A promising new method to select novel zinc-finger arrays utilizes a bacterial two-hybrid system that combines pre-selected pools of individual zinc finger repeats that were each selected to bind a given triplet and then utilizes a second round of selection to obtain 3-finger repeats capable of binding a desired 9-bp sequence (Maeder M L, et al., "Rapid 'open-source' engineering of customized zinc-finger nucleases for highly efficient gene modification". Mol. Cell (2008) 31(2): 294-301). The non-specific cleavage domain from the type II restriction endonuclease FokI is typically used as the cleavage domain in ZFNs. This cleavage domain must dimerize in order to cleave DNA and thus a pair of ZFNs are required to target non-palindromic DNA sites. Standard ZFNs fuse the cleavage domain to the C-terminus of each zinc finger domain. In order to allow the two cleavage domains to dimerize and cleave DNA, the two individual ZFNs must bind opposite strands of DNA with their C-termini a certain distance apart. The most commonly used linker sequences between the zinc finger domain and the cleavage domain requires the 5' edge of each binding site to be separated by 5 to 7 bp.

Methods of Generating Donor DNA

It has recently been reported that using single-stranded DNA as donor can increase the efficiency of target insertion mediated by homologous recombination (Quadros et al., "Easi-CRISPR: a robust method for one-step generation of mice carrying conditional and insertion alleles using long ssDNA donors and CRISPR ribonucleoproteins" Genome Biology (2017) 18:92). Generating long ssDNA suitable as donor nucleic acid, however, has been a problem because long ssDNA is unstable and the size of ssDNA generated by chemical synthesis is limited to about 200 nucleotides. Therefore, in one aspect, the present disclosure provides methods for generating donor DNA used for targeted insertion with increased efficiency.

One of the exemplary examples of the methods is illustrated in FIG. 1. Referring to FIG. 1, in order to generate an ssDNA as donor for inserting a nucleotide sequence (gene of interest) to a specific target locus in the genome of a cell, a polynucleotide typically in the form of double-stranded DNA is generated to comprise the gene of interest flanked by homologous arms corresponding to the target locus. A pair of primers is then used to amplify the polynucleotide using polymerase chain reaction (PCR). One of the primers used for the amplification contains at least one modification that is resistant to an exonuclease. In certain embodiments, the modification is biotinylation, 5' hydroxy group, phosphorothioate bond, 2'-O-methyl base or 2'fluoro base. In certain embodiments, the modification is at the 5' end of the primer. In certain embodiments, the modification is at a nucleotide in the middle of the primer. In certain embodiments, the exonuclease is lambda exonuclease, T5 exonuclease or T7 exonuclease. The PCR product (i.e., amplicon) is then treated with the exonuclease to digest polynucleotides that do not have the modification. The digested product is ssDNA that contains the exonuclease resistant modification and comprises the gene of interest flanked by homologous arms.

Figure 2:
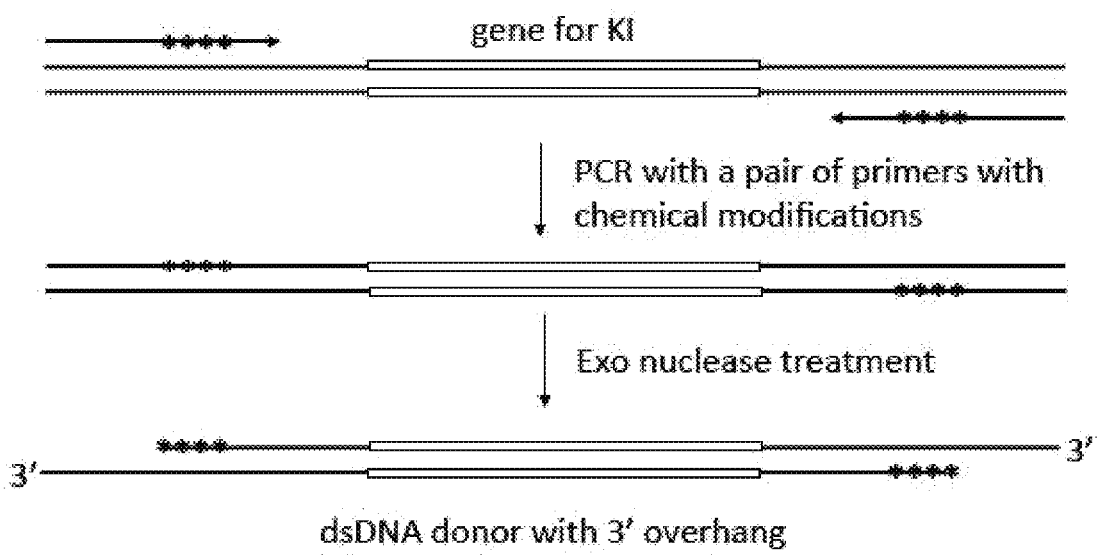
FIG. 2 illustrates an exemplary example of the methods for generating the dsDNA donor for targeted insertion.

In addition to ssDNA, we found dsDNA with 3' ssDNA overhang can also be used as a donor for targeted insertion with increased efficiency. FIG. 2 illustrates an exemplary example of the methods of making such dsDNA with 3' ssDNA overhang. Now referring to FIG. 2, a polynucleotide typically in the form of double-stranded DNA is generated to comprise the gene of interest flanked by homologous arms corresponding to the target locus. A pair of primers is then used to amplify the polynucleotide using PCR. Both of the primers used for the amplification contains at least one modification that is resistant to an exonuclease. In certain embodiments, the exonuclease resistant modification is at a nucleotide in the middle, e.g., the $5^{th}$ to $200^{th}$ nucleotide from the 5' end of the primers. The PCR product is then treated with the exonuclease, which results a dsDNA with 3' overhang of 5-200 nucleotides.

In another example, a dsDNA with 3' end ssDNA overhang can also be made by annealing two strands of partially complementary dsDNA. The dsDNA can be made using the method illustrated in FIG. 1.

Compositions and Methods for Gene Editing

The ssDNA and the dsDNA with 3' ssDNA overhang generated using the methods provided herein can be used to insert the gene of interest to a target locus of the genome in a cell. Therefore, in another aspect, the present disclosure provides compositions and methods for targeted DNA insertion.

In certain embodiments, the composition comprise (i) a site-specific nuclease or a nucleic acid encoding the same; and (ii) the ssDNA or the dsDNA with 3' end overhang provided herein. In certain embodiments, the site-specific nuclease is Cas9, a zinc finger nuclease or a TALEN.

In certain embodiments, the method for gene editing in a cell comprises introducing into the cell (i) a site-specific nuclease or a nucleic acid encoding the same; and (ii) the ssDNA or dsDNA with 3' end overhang as provided herein.

In certain embodiments, the site-specific nuclease introduced into the cell creates a double-strand break (DSB) at the target locus. The DSB created can be repaired by a repair processes such as the non-homologous end joining (NHEJ) pathway or the homology-directed repair (HDR) (see Moore J K, Haber J E, 1996. "Cell cycle and genetic requirements of two pathways of nonhomologous end-joining repair of double-strand breaks in *Saccharomyces cerevisiae*". 16 (5): 2164-73.). While HDR refers to the process of repairing DNA damage using a homologous nucleic acid (e.g., an endogenous homologous sequence, e.g., a sister chromatid, or an exogenous nucleic acid, e.g., a template nucleic acid), there are two types of HDR, canonical HDR and alternative HDR. Typically, canonical HDR functions when there has been significant resection at the double-strand break, forming at least one single stranded portion of DNA. Alternative HDR (i.e. Alt-HDR) refers to the process of repairing DNA damage using a homologous nucleic acid (e.g., an endogenous homologous sequence, e.g., a sister chromatid, or an exogenous nucleic acid, e.g., a template nucleic acid). Alt-HDR differs from canonical HDR in that the process utilizes different pathways from canonical HDR, and can be inhibited by the canonical HDR mediators, RAD51 and BRCA2. Alt-HDR uses a single-stranded or nicked homologous nucleic acid for repair of the break.

The gene of interest as used herein can be any polynucleotide sequence. In certain embodiments, the gene of interest comprises a polynucleotide sequence encoding proteins include, but not limited to, proteins selected from the group consisting of: alpha-1 antitrypsin, angiostatin, antihemolytic factor, antibody, antibody fragments, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor 1, soluble I-CAM 1, soluble interleukin receptor, soluble TNF receptor, somatomedin, somatostatin, somatotropin, streptokinase, super-antigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

Example 1

Figure 3:
FIG. 3 illustrates the generation of ssDNA using lambda exonuclease. dsDNA template was amplified by PCR with modified primers. The first six bases of the forward primer were modified with phosphorothioate and the 5' end of the reverse primer was phosphorylated. The template contains short homologous arms of mouse Oprm gene and a HaloTag. The purified PCR product was digested with lambda exonuclease for 30 minutes at 37° C. Lane1: 1 kb Marker, Lane2: double-stranded PCR product, Lane3: single-stranded DNA generated with lambda exonuclease from the double-stranded PCR product.

This example illustrates the generation of ssDNA using lambda exonuclease.

dsDNA template was amplified by PCR with modified primers. The first six bases of the forward primer were modified with phosphorothioate and the 5' end of the reverse primer was phosphorylated (The primers were synthesized by Integrated DNA Technologies, Coralville, Iowa. The forward primer was SEQ ID NO: 1, C*C*T*A*G*G*GCAGCTGTGAGAGG, where * indicated phosphorothioate modification. The reverse primer SEQ ID NO: 2, CGTGGGACAAGTTGAGCCAGG was phosphorylated at the 5' end.). The template contains a 103 bp arm at the 5' end and 82 bp arm at the 3' end homologous to mouse Oprm gene. A the knockin fragment was a HaloTag. The purified PCR product (SEQ ID NO: 3) was digested with lambda exonuclease (New England Biolabs) for 30 minutes at 37° C. and ran an electrophoresis. The result is shown in FIG. 3. Lane1: 1 kb Marker, Lane2: double-stranded PCR product, Lane3: single-stranded DNA generated with lambda exonuclease from the double-stranded PCR product.

Example 2

Figure 4:
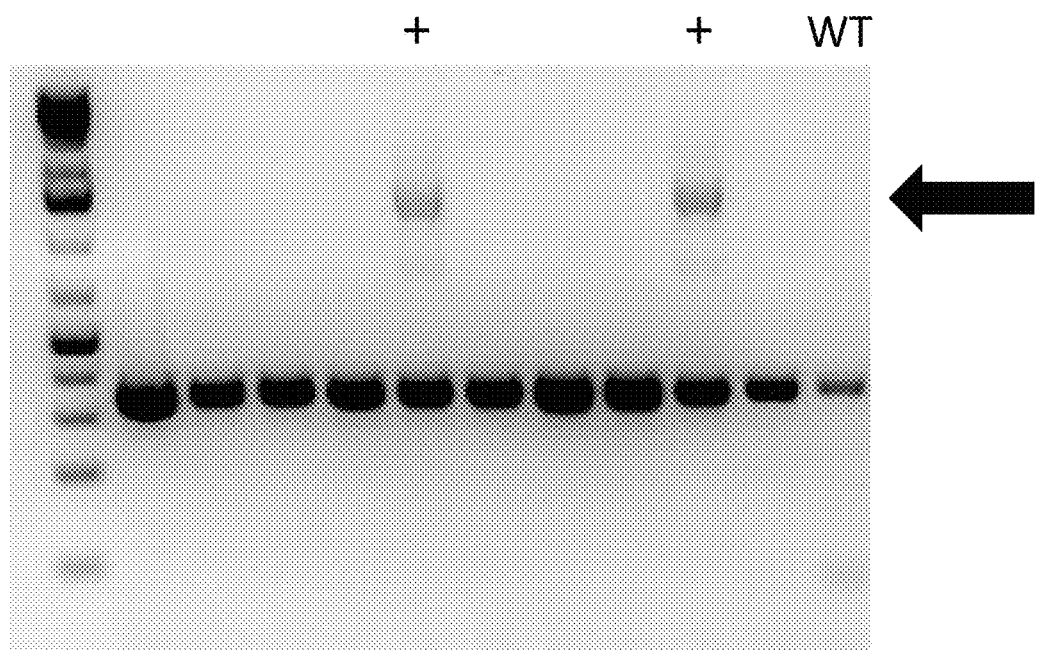
FIG. 4 illustrates the generation of knock-in mouse with ssDNA template. ssDNA template generated in FIG. 3 was gel purified and used for single embryo microinjection together with gRNA and Cas9 protein targeting the mouse Oprm gene. Genomic DNA from the pups were used for genotyping by PCR. Gel electrophoresis indicated two out of 10 pups with right knockin (1.4 kb PCR fragment, arrow). Left lane: 1 kb Marker. The bottom 350 bp PCR fragment was from the wild type allele.

This example illustrates the generation of knock-in mouse with ssDNA template. ssDNA template generated in Example 1 was gel purified and used for single mouse embryo microinjection. The microinjection cocktail was made up with ssDNA at 10 ng/ul, in vitro transcribed guide RNA at 20 ng/ul and Cas9 protein at 20 ng/ul. Total of 106 embryos were injected and 21 pups were born alive. Genomic DNA from 10 pups were used for genotyping by PCR. As shown in FIG. 4, Gel electrophoresis indicated two out of 10 pups with right knockin (1.4 kb PCR fragment, arrow). Left lane: 1 kb Marker. The bottom 350 bp PCR fragment was from the wild type allele.

What is claimed is:

1. A method for inserting a gene of interest to a target locus in a mouse embryo, the method comprising:
   (a) amplifying the gene of interest using a pair of primers to generate a double-stranded DNA (dsDNA) amplicon, wherein one of the pair of primers has an exonuclease resistant modification that is resistant to an exonuclease;
   (b) treating the dsDNA amplicon with the exonuclease, thereby generating a single-stranded DNA (ssDNA) comprising the gene of interest; and
   (c) introducing into the mouse embryo a composition comprising:
      (c1) the ssDNA of about 10 ng/ul,
      (c2) a Cas9 protein of about 20 ng/ul, or a nucleic acid encoding the same, and
      (c3) a guide RNA directed to the target locus of about 20 ng/ul,
   thereby introducing the gene of interest to the target locus in the mouse embryo, wherein the target locus is Oprm gene, and the ssDNA contains a 103 bp arm at the 5' end and 82 bp arm at the 3' end homologous to mouse Oprm gene.

2. The method of claim 1, wherein the exonuclease resistant modification is biotinylation, 5' hydroxy group, phosphorothioate bond, 2'-O-methyl base or 2'fluoro base.

3. The method of claim 1, wherein the exonuclease resistant modification is resistant to lambda exonuclease, T5 exonuclease or T7 exonuclease.

4. The method of claim 1, wherein the composition is introduced to the embryo via microinjection.

5. The method of claim 1, further comprising developing the mouse embryo into a mouse pup.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cctagggcag ctgtgagagg                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
cgtgggacaa gttgagccag g                                            21
```

```
<210> SEQ ID NO 3
<211> LENGTH: 1232
<212> TYPE: DNA
<213> ORGANISM: Artificial Sequence
<220> FEATURE:
<223> OTHER INFORMATION: Synthetic

<400> SEQUENCE: 3
cctagggcag ctgtgagagg aagaggctgg ggcgcctgga acccgaacac tcttgagtgc      60
tctcagttac agcctaccga gtccgcagca agcattcaga accatggctc ttctgttgat     120
cctgtcagtc ctacttctga aagaagatgt acgagggagt gcacagtcca cgcgataccc     180
ctacgacgtg cccgactacg ccacgcgagg atccaccggt gaattcacca tggcagaaat     240
cggtactggc tttccattcg accccatta tgtggaagtc ctgggcgagc gcatgcacta      300
cgtcgatgtt ggtccgcgcg atggcacccc tgtgctgttc ctgcacggta acccgacctc     360
ctcctacgtg tggcgcaaca tcatcccgca tgttgcaccg acccatcgct gcattgctcc     420
agacctgatc ggtatgggca aatccgacaa accagacctg ggttatttct tcgacgacca     480
cgtccgcttc atggatgcct tcatcgaagc cctgggtctg gaagaggtcg tcctggtcat     540
tcacgactgg ggctccgctc tgggtttcca ctgggccaag cgcaatccag agcgcgtcaa     600
aggtattgca tttatggagt tcatccgccc tatcccgacc tgggacgaat ggccagaatt     660
tgcccgcgag accttccagg ccttccgcac caccgacgtc ggccgcaagc tgatcatcga     720
tcagaacgtt tttatcgagg gtacgctgcc gatgggtgtc gtccgcccgc tgactgaagt     780
cgagatggac cattaccgcg agccgttcct gaatcctgtt gaccgcgagc cactgtggcg     840
cttcccaaac gagctgccaa tcgccggtga gccagcgaac atcgtcgcgc tggtcgaaga     900
atacatggac tggctgcacc agtcccctgt cccgaagctg ctgttctggg caccccagg      960 cgttctgatc ccaccggccg aagccgctcg cctggccaaa agcctgccta actgcaaggc    1020
tgtggacatc ggcccgggtc tgaatctgct gcaagaagac aacccggacc tgatcggcag    1080
cgagatcgcg cgctggctgt cgacgctcga gatttccggc cctgcaggag atgacagcag    1140
cgccggccca gggaacatca gcgactgctc tgacccctta gctcctgcaa gttgctcccc    1200
agcacctggc tcctggctca acttgtccca cg                                   1232
```